US00PP26660P2

(12) United States Plant Patent
Meinl

(10) Patent No.: US PP26,660 P2
(45) Date of Patent: Apr. 26, 2016

(54) ***HYDRANGEA* PLANT NAMED 'SAXLIMAR'**

(50) Latin Name: *Hydrangea macrophylla*
Varietal Denomination: Saxlimar

(71) Applicant: Katrin Meinl, Dresden (DE)

(72) Inventor: Katrin Meinl, Dresden (DE)

(73) Assignee: Kühne Jungpflanzen Claus + Torsten Kühne Gbr, Dresden (DE)

( * ) Notice: Subject to any disclaimer, the term of this patent is extended or adjusted under 35 U.S.C. 154(b) by 90 days.

(21) Appl. No.: 14/120,669

(22) Filed: Jun. 14, 2014

(51) Int. Cl.
*A01H 5/02* (2006.01)

(52) U.S. Cl.
USPC ..... Plt./250

(58) Field of Classification Search
USPC ..... Plt./250
See application file for complete search history.

*Primary Examiner* — Anne Grunberg
(74) *Attorney, Agent, or Firm* — C. A. Whealy

(57) ABSTRACT

A new and distinct cultivar of *Hydrangea* plant named 'Saxlimar', characterized by its upright and mounded plant habit; moderately vigorous growth habit; strong stems; and large mophead-type inflorescences that when treated with aluminum sulfate have bright blue-colored sterile flowers with a fine whitish-colored margin.

2 Drawing Sheets

Botanical designation: *Hydrangea macrophylla.*
Cultivar denomination: 'SAXLIMAR'.

BACKGROUND OF THE INVENTION

The present invention relates to a new and distinct cultivar of *Hydrangea* plant, botanically known as *Hydrangea macrophylla* and hereinafter referred to by the name 'Saxlimar'.

The new *Hydrangea* plant is a product of a planned breeding program conducted by the Inventor in Dresden, Germany. The objective of the breeding program was to develop new container-type *Hydrangea* plants with strong stems, early flowering response and attractive leaf, stem and flower coloration.

The new *Hydrangea* plant originated from a cross-pollination in 2009 of *Hydrangea macrophylla* 'Horpill', disclosed in U.S. Plant Pat. No. 19,761, as the female, or seed parent and an unidentified proprietary selection of *Hydrangea macrophylla,* not patented, as the male, or pollen, parent. The new *Hydrangea* plant was discovered and selected by the Inventor in 2011 as a flowering plant within the progeny of the stated cross-pollination in a controlled environment in Dresden, Germany.

Asexual reproduction of the new cultivar by softwood cuttings in Dresden, Germany since June, 2011 has shown that the unique features of this new *Hydrangea* plant are stable and reproduced true to type in successive generations of asexual reproduction.

SUMMARY OF THE INVENTION

Plants of the new *Hydrangea* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Saxlimar'.

These characteristics in combination distinguish 'Saxlimar' as a new and distinct *Hydrangea* plant:

1. Upright and mounded plant habit.
2. Moderately vigorous growth habit.
3. Strong stems.
4. Large mophead-type inflorescences that when treated with aluminum sulfate have bright blue-colored sterile flowers with a fine whitish-colored margin.

Plants of the new *Hydrangea* differ primarily from plants of the female parent, 'Horpill', in the following characteristics:

1. Plants of the new *Hydrangea* have stronger stems than plants of 'Horpill'.
2. Plants of the new *Hydrangea* have larger leaves than plants of 'Horpill'.
3. When treated with aluminum sulfate, plants of the new *Hydrangea* and 'Horpill' differ in sterile flower color as plants of 'Horpill' have violet-colored flowers.

Plants of the new *Hydrangea* differ primarily from plants of the male parent selection in plant habit as plants of the new *Hydrangea* are more compact than plants of the male parent selection.

Plants of the new *Hydrangea* can be compared to plants of *Hydrangea macrophylla* 'Bavaria', not patented. Plants of the new *Hydrangea* differ primarily from plants of 'Bavaria' in the following characteristics:

1. Plants of the new *Hydrangea* have stronger stems than plants of 'Bavaria'.
2. Plants of the new *Hydrangea* have larger leaves than plants of 'Bavaria'.
3. Plants of the new *Hydrangea* and 'Bavaria' differ slightly in sterile flower color as plants of 'Bavaria' have broader white-colored margins on the sepals.
4. Inflorescences of plants of the new *Hydrangea* are more high temperature tolerant than inflorescences of plants of 'Bavaria'.

BRIEF DESCRIPTION OF THE PHOTOGRAPHS

The accompanying colored photographs illustrate the unique appearance of the new *Hydrangea* plant showing the colors as true as it is reasonably possible to obtain in colored reproductions of this type. Colors in the photographs may differ from the color values cited in the detailed botanical description which accurately describe the colors of the new *Hydrangea* plant.

The photograph on the first sheet comprises a side perspective view of a typical flowering plant of 'Saxlimar' grown in a container.

The photograph on the second sheet is a close-up view of a typical inflorescence of 'Saxlimar'.

DETAILED BOTANICAL DESCRIPTION

Plants used in the aforementioned photographs and in the following description were grown in 3-liter containers in a glass-covered greenhouse in Dresden, Germany and under cultural conditions typical of commercial *Hydrangea* production conditions. Plants of the new *Hydrangea* were two years old when the photographs and description were taken. During the production of the plants, day temperatures ranged from 18° C. to 25° C. and night temperatures ranged from 16° C. to 17° C. Plants were treated with aluminum sulfate to "blue" the inflorescences. In the following description, color references are made to The Royal Horticultural Society Colour Chart, 2007 Edition, except where general terms of ordinary dictionary significance are used.

Botanical description: *Hydrangea macrophylla* 'Saxlimar'.

Parentage:

- *Female, or seed, parent.*—*Hydrangea macrophylla* 'Horpill', disclosed in U.S. Plant Pat. No. 19,761.
- *Male, or pollen, parent.*—Unidentified proprietary selection of *Hydrangea macrophylla,* not patented.

Propagation:

- *Type cutting.*—By softwood cuttings.
- *Time to initiate roots, summer.*—About 15 days at temperatures about 18° C.
- *Time to initiate roots, winter.*—About 17 days at temperatures about 18° C.
- *Time to produce a rooted young plant, summer.*—About 29 days at temperatures about 18° C.
- *Time to produce a rooted young plant, winter.*—About 31 days at temperatures about 18° C.
- *Root description.*—Fine, fibrous; white to grey in color.
- *Rooting habit.*—Moderately freely branching; sparse.

Plant description:

- *Plant and growth habit.*—Perennial subshrub; upright and mounded plant habit; broadly inverted triangle; freely branching habit with about twelve lateral branches developing per plant; strong lateral branches; moderately vigorous growth habit.
- *Plant height.*—About 31.4 cm.
- *Plant diameter or area of spread.*—About 46.5 cm.
- *Lateral branches.*—Length: About 16.9 cm. Diameter: About 6 mm. Internode length: About 4 cm. Texture: Smooth, glabrous. Strength: Strong. Aspect: About 45° from vertical. Color, developing: Close to 143C; at the nodes, slightly tinged with close to N186C. Color, developed: Close to 199B. Lenticels: Density: Moderate. Length: About 1.5 mm. Diameter: About 0.75 mm. Color: Close to N186C.

Leaf description:

- *Arrangement.*—Opposite, simple.
- *Length.*—About 11.4 cm.
- *Width.*—About 8.8 cm.
- *Shape.*—Broadly ovate.
- *Apex.*—Broadly apiculate.
- *Base.*—Rounded to short attenuate.
- *Margin.*—Serrate.
- *Texture, upper surface.*—Smooth, glabrous.
- *Texture, lower surface.*—Smooth, glabrous.
- *Venation pattern.*—Pinnate.
- *Color.*—Developing leaves, upper surface: Darker than 143A. Developing leaves, lower surface: Close to 146D. Fully expanded leaves, upper surface: Darker than between 139A and 147A; venation, close to 144A. Fully expanded leaves, lower surface: Close to between 137C and 147B; venation, close to 144A to 144B.
- *Petioles.*—Length: About 2.1 cm. Diameter: About 4 mm. Texture, upper and lower surfaces: Smooth, glabrous. Color, upper and lower surfaces: Close to 144A.

Inflorescence & flower description:

- *Flower type and habit.*—Single sterile and inconspicuous fertile flowers arranged on terminal mophead-type panicles; panicles flattened globular in overall shape; fertile flowers face mostly upright and sterile flowers face upright to outwardly.
- *Fragrance.*—Faintly fragrant, pleasant.
- *Natural flowering season.*—Continuous flowering from late spring to late summer in The Netherlands.
- *Flower longevity, fertile flowers.*—Flowers last about one week on the plant; flowers not persistent.
- *Flower longevity, sterile flowers.*—Flowers last about six weeks on the plant; flowers persistent.
- *Quantity of flowers.*—Freely flowering; about 120 fertile flowers and about 400 sterile flowers per panicle.
- *Panicle height.*—About 10.3 cm.
- *Panicle diameter.*—About 17.8 cm.
- *Flower diameter, fertile flowers.*—About 8 mm.
- *Flower depth (height), fertile flowers.*—About 4 mm.
- *Flower diameter, sterile flowers.*—About 3.5 cm.
- *Flower depth (height), sterile flowers.*—About 1 cm.
- *Flower buds, fertile flowers.*—Length: About 3 mm. Diameter: About 3.5 mm. Shape: Flattened globular. Color: Close to 115C.
- *Flower buds, sterile flowers.*—Length: About 1 cm. Diameter: About 8 mm. Shape: Ovoid. Color: Close to 100C.
- *Petals, fertile flowers only.*—Quantity and arrangement: Four, occasionally five in a single whorl. Length: About 2.5 mm. Width: About 1.5 mm. Shape: Ovate, concave. Apex: Broadly acute. Base: Cuneate. Margin: Entire. Texture, upper and lower surfaces: Smooth, glabrous. Color: When opening and fully opened, upper surface: Close to 104B. When opening and fully opened, lower surface: Close to 104B.
- *Sepals, fertile flowers.*—Quantity and arrangement: Five in a single whorl. Length: About 1.5 mm. Width: About 0.75 mm. Shape: Broadly ovate to narrowly deltoid. Apex: Acute. Base: Broadly cuneate. Margin: Entire. Texture, upper and lower surfaces: Smooth, glabrous. Color, upper and lower surfaces: Close to 145C; apex tinged with close to 100B.
- *Sepals, sterile flowers.*—Quantity and arrangement: Four or five in a single whorl. Length: About 1.9 cm. Width: About 2 cm. Shape: Broadly rhomboidal to broadly ovate. Apex: Bluntly acute. Base: Broadly cuneate. Margin: Entire. Texture, upper and lower surfaces: Smooth, glabrous. Color: When opening, upper surface: Close to 98A. When opening, lower surface: Close to 98B to 98C. Fully opened, upper surface: Close to 99D; fine margin, whitish; with development, color becoming closer to 93B tinged with close to 96A to 96B. Fully opened, lower surface: Close to 98B to 98C; with development, color becoming closer to 97A tinged with close to 94C.

*Pedicels, fertile flowers*.—Angle: About 20° from vertical. Strength: Moderately strong. Length: About 3 mm. Diameter: About 1 mm. Texture: Smooth, glabrous. Color: Close to 66B.

*Pedicels, sterile flowers*.—Angle: About 30° from lateral branch. Strength: Strong. Length: About 1.9 cm. Diameter: About 1.5 mm. Texture: Smooth, glabrous. Color: Close to 100C.

*Reproductive organs, fertile flowers only*.—Stamens: Quantity per flower: About ten. Filament length: About 2 mm. Filament color: Close to 104B. Anther length: About 1 mm. Anther shape: Broadly reniform. Anther color: Close to 126D. Pollen amount: Moderate. Pollen color: Close to 156D. Pistils: Pistil quantity per flower: About three. Pistil length: About 1 mm. Stigma shape: Club-shaped. Stigma color: Close to 145C to 145D. Style length: About 0.5 mm. Style color: Close to 145A to 145B. Ovary color: Close to 157D.

*Seeds and fruits*.—Seed and fruit development have not been observed on plants of the new *Hydrangea* to date.

Disease & pest resistance: Plants of the new *Hydrangea* have not been observed to be resistant to pathogens and pests common to *Hydrangea* plants.

Temperature tolerance: Plants of the new *Hydrangea* have been shown to be tolerant to temperatures in USDA Hardiness Zones 5 to 9.

It is claimed:

1. A new and distinct *Hydrangea* plant named 'Saxlimar' as illustrated and described.

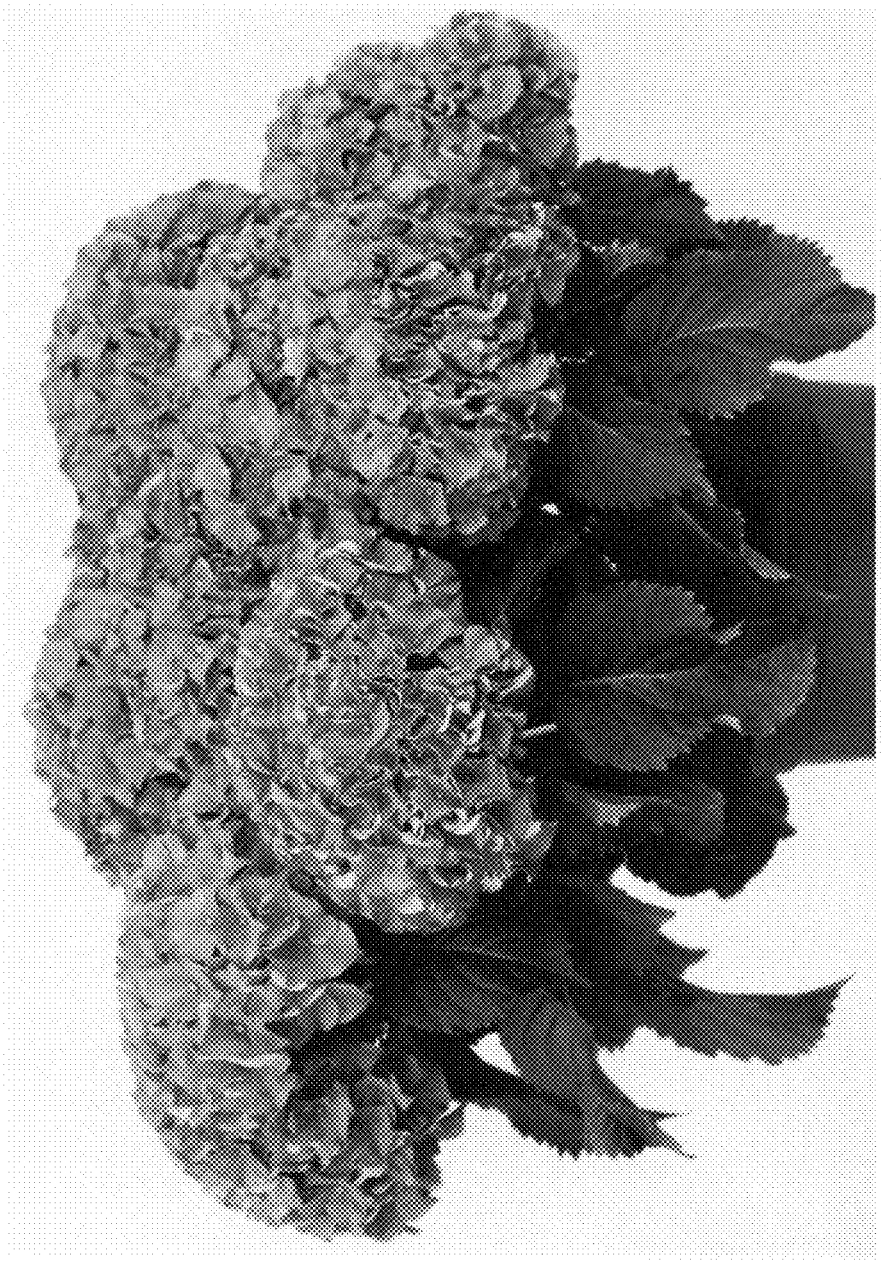

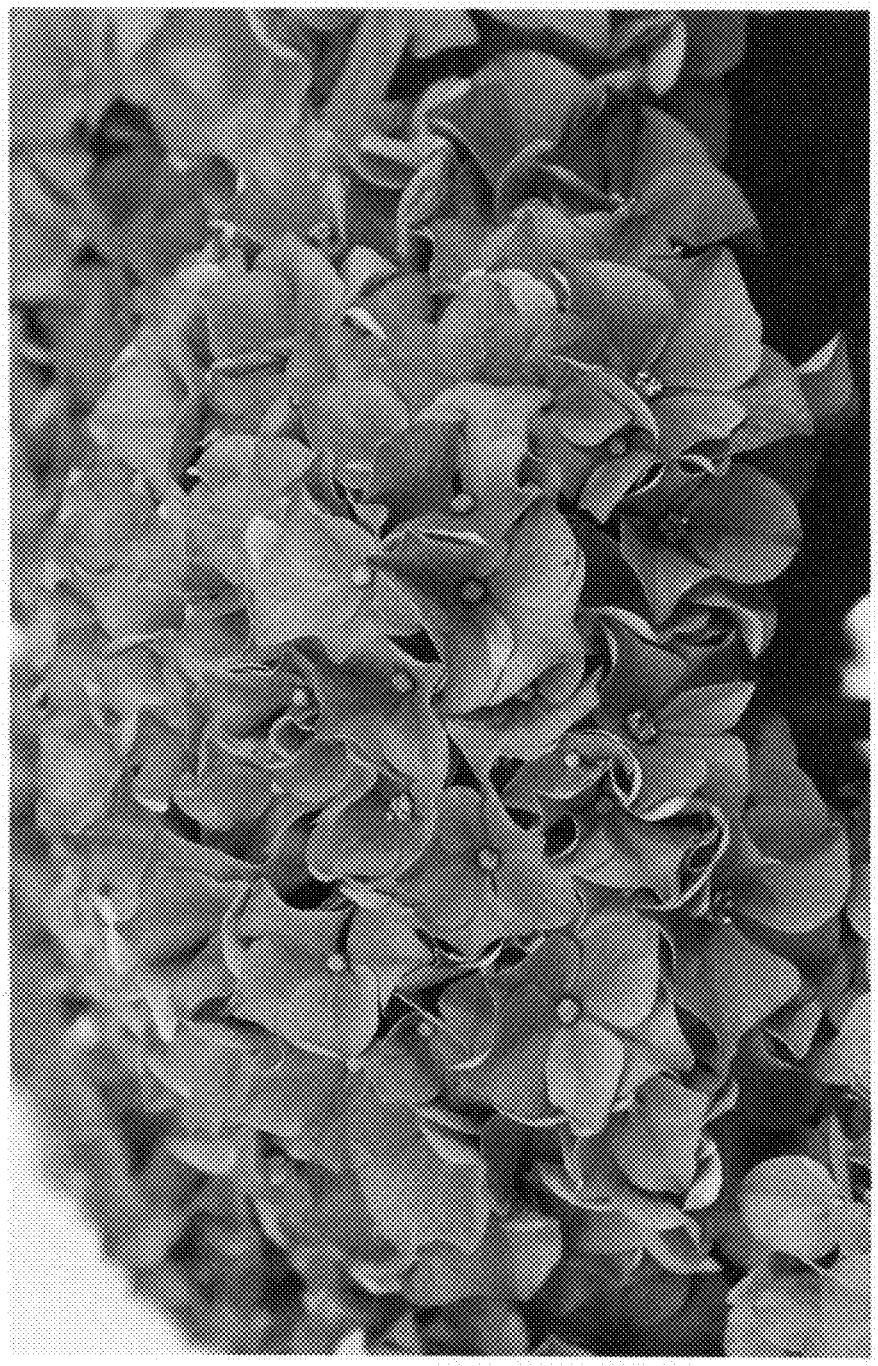

* * * * *